(12) United States Patent  (10) Patent No.: US 10,940,067 B2
Hashimoto  (45) Date of Patent: Mar. 9, 2021

(54) ROBOT SYSTEM

(71) Applicant: KAWASAKI JUKOGYO KABUSHIKI KAISHA, Kobe (JP)

(72) Inventor: Yasuhiko Hashimoto, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 416 days.

(21) Appl. No.: 15/741,054

(22) PCT Filed: Jun. 29, 2015

(86) PCT No.: PCT/JP2015/003251
§ 371 (c)(1),
(2) Date: Dec. 29, 2017

(87) PCT Pub. No.: WO2017/002142
PCT Pub. Date: Jan. 5, 2017

(65) Prior Publication Data
US 2018/0185219 A1  Jul. 5, 2018

(51) Int. Cl.
*A61G 7/018* (2006.01)
*A61G 13/00* (2006.01)
(Continued)

(52) U.S. Cl.
CPC .............. *A61G 7/018* (2013.01); *A61B 34/30* (2016.02); *A61B 90/50* (2016.02); *A61G 5/006* (2013.01);
(Continued)

(58) Field of Classification Search
CPC ........ A61G 7/018; A61G 13/00; A61G 7/075; A61G 7/015; A61G 5/14; A61G 5/006;
(Continued)

(56) References Cited

U.S. PATENT DOCUMENTS 7,076,818 B2 * 7/2006 Kummer ................. A61G 7/00
5/424
9,254,234 B2 * 2/2016 Cooper ............... A61G 7/1017
(Continued)

FOREIGN PATENT DOCUMENTS

JP  2009-213892 A  9/2009
JP  2012-501866 A  1/2012
(Continued)

OTHER PUBLICATIONS

Aug. 4, 2015 International Search Report issued in International Patent Application No. PCT/JP2015/003251.
(Continued)

*Primary Examiner* — Peter M. Cuomo
*Assistant Examiner* — Myles A Throop
(74) *Attorney, Agent, or Firm* — Oliff PLC

(57) ABSTRACT

A robot system includes: at least one supporting unit, on which a person is placeable; a robot including a plurality of multi-jointed arms, each of which has a plurality of degrees of freedom, and at least one base provided with the plurality of multi-jointed arms; and at least one type of equipment mountable to the plurality of multi-jointed arms. The robot performs at least two nursing/medical actions on the person by operating the at least one type of equipment.

13 Claims, 14 Drawing Sheets

(51) Int. Cl.
*B25J 9/06* (2006.01)
*A61B 34/30* (2016.01)
*A61B 90/50* (2016.01)
*A61G 5/00* (2006.01)
*A61G 5/14* (2006.01)
*A61G 7/015* (2006.01)
*A61G 7/075* (2006.01)
*B25J 9/00* (2006.01)
*B25J 15/00* (2006.01)

(52) U.S. Cl.
CPC ............... *A61G 5/14* (2013.01); *A61G 7/015* (2013.01); *A61G 7/075* (2013.01); *A61G 13/00* (2013.01); *B25J 9/0087* (2013.01); *B25J 9/0096* (2013.01); *B25J 9/06* (2013.01); *B25J 15/0019* (2013.01); *B25J 15/0028* (2013.01); *Y10S 901/01* (2013.01); *Y10S 901/15* (2013.01); *Y10S 901/31* (2013.01); *Y10S 901/44* (2013.01)

(58) Field of Classification Search
CPC .............. A61G 2203/18; A61G 7/1082; A61G 7/1017; B25J 9/06; B25J 9/0096; B25J 9/0087; B25J 15/0028; B25J 15/0019; B25J 13/00; A61B 90/50; A61B 34/30; Y10S 901/44; Y10S 901/31; Y10S 901/15; Y10S 901/01
USPC ...................................... 5/616; 700/245–264
See application file for complete search history.

(56) References Cited

U.S. PATENT DOCUMENTS

| | | | |
|---|---|---|---|
| 9,814,640 B1* | 11/2017 | Khaligh | A61G 7/05 |
| 2001/0032362 A1* | 10/2001 | Welling | A61G 7/0528 5/600 |
| 2007/0289064 A1* | 12/2007 | Martin | A61G 7/012 5/618 |
| 2009/0055019 A1* | 2/2009 | Stiehl | B25J 9/1671 700/249 |
| 2009/0234444 A1 | 9/2009 | Maschke | |
| 2010/0069920 A1* | 3/2010 | Naylor | A61B 34/71 606/130 |
| 2011/0029133 A1 | 2/2011 | Okazaki et al. | |
| 2011/0087416 A1* | 4/2011 | Patmore | A61G 1/048 701/93 |
| 2012/0023660 A1* | 2/2012 | Ota | A61G 7/1019 5/81.1 R |
| 2014/0188129 A1 | 7/2014 | Kang | |
| 2014/0350571 A1 | 11/2014 | Maillet et al. | |

FOREIGN PATENT DOCUMENTS

| | | |
|---|---|---|
| JP | 5481110 B2 | 4/2014 |
| JP | 2015-085406 A | 5/2015 |
| WO | 2009/147832 A1 | 12/2009 |

OTHER PUBLICATIONS

Mar. 5, 2020 Office Action issued in Chinese Patent Application No. 201580080711.7.

* cited by examiner

ROBOT SYSTEM

TECHNICAL FIELD

The present invention relates to a robot system for performing nursing/medical actions.

BACKGROUND ART

Conventionally, various robots for performing nursing/medical actions on a person have been proposed. For example, FIG. 19 of Patent Literature 1 discloses a dual-arm nursing robot for lifting a person lying on a bed.

CITATION LIST

Patent Literature

PTL 1: WO 2009/147832

SUMMARY OF INVENTION

Technical Problem

Such a conventional nursing/medical care robot is designed such that it is dedicated for a particular nursing/medical action. Therefore, in order to perform a plurality of nursing/medical actions, the same number of robots as the number of the plurality of nursing/medical actions is necessary.

In view of the above, an object of the present invention is to provide a robot system including a single robot that is capable of performing a plurality of nursing/medical actions.

Solution to Problem

In order to solve the above-described problems, a robot system of the present invention includes: at least one supporting unit, on which a person is placeable; a robot including a plurality of multi-jointed arms, each of which has a plurality of degrees of freedom, and at least one base provided with the plurality of multi-jointed arms; and at least one type of equipment mountable to the plurality of multi-jointed arms. The robot performs at least two nursing/medical actions on the person by operating the at least one type of equipment.

According to the above configuration, the robot can be used as a platform for a plurality of nursing/medical actions. This makes it possible to perform the plurality of nursing/medical actions with the single robot.

The at least one type of equipment may include a pair of transmission inspection devices that are mounted to two multi-jointed arms, respectively, of the plurality of multi-jointed arms, and the at least two nursing/medical actions may include an action of performing a transmission inspection on the person. According to this configuration, the robot can be used in common for the action of performing the transmission inspection on the person and the other nursing/medical action(s).

The at least one supporting unit may include a transformable bed partly swingable in its width direction. The at least one type of equipment may include a hand configured to operate the transformable bed. The at least two nursing/medical actions may include an action of changing a body position of the person via the transformable bed to change a position where the person is in contact with the transformable bed. According to this configuration, the robot can be used in common for the action of changing the body position and the other nursing/medical action(s).

The at least one supporting unit may include a transformable bed transformable between a bed mode and a chair mode. The at least one type of equipment may include a hand configured to operate the transformable bed. The at least two nursing/medical actions may include an action of raising an upper half of a body of the person via the transformable bed to change a state of the person from a lying-down state into a sitting state. According to this configuration, the robot can be used in common for the action of raising the upper half of the body and the other nursing/medical action(s).

The above robot system may further include an armrest attached to at least one of the plurality of multi-jointed arms. The at least two nursing/medical actions may include an action of performing standing-up motion assistance to the person to support the person with the armrest until the person in the sitting state stands up. According to this configuration, the robot can be used in common for, at least, the action of raising the upper half of the body and the action of performing the standing-up motion assistance.

For example, the at least one type of equipment may include a plurality of types of equipment, and each type of equipment may be removably mounted to the plurality of multi-jointed arms.

The at least one supporting unit may be coupled to the at least one base. According to this configuration, the position of the supporting unit relative to the base of the robot is fixed. This makes it possible to readily perform the positioning of the equipment, which is mounted to the multi-jointed arms, relative to the person or the supporting unit.

The at least one base may be disposed under the supporting unit, such that an entirety of the at least one base is accommodated within a space occupied by the supporting unit. According to this configuration, since the relatively large base of the robot is concealed under the supporting unit, anyone around the supporting unit can freely come close to the person placed on the supporting unit. This allows anyone around the supporting unit to readily perform a procedure/treatment on the person placed on the supporting unit.

The robot may be configured such that the plurality of multi-jointed arms are retractable under the at least one supporting unit. According to this configuration, when the robot performs no nursing/medical action, the multi-jointed arms can be retracted under the supporting unit, and the robot can be stored under the supporting unit.

For example, the robot may be configured to perform each of the at least two nursing/medical actions in accordance with a sound or an operation of a switch, and the robot may be configured to repeat the action of changing the body position of the person at predetermined intervals.

The above robot system may further include a moving device incorporated in the base, the moving device including a pair of servomotors configured to drive right and left wheels. The robot may be moved by controlling the pair of servomotors by a robot control board. This configuration makes it possible to freely run the robot.

Advantageous Effects of Invention

The present invention makes it possible to perform a plurality of nursing/medical actions with a single robot.

DESCRIPTION OF EMBODIMENTS

Figure 1:
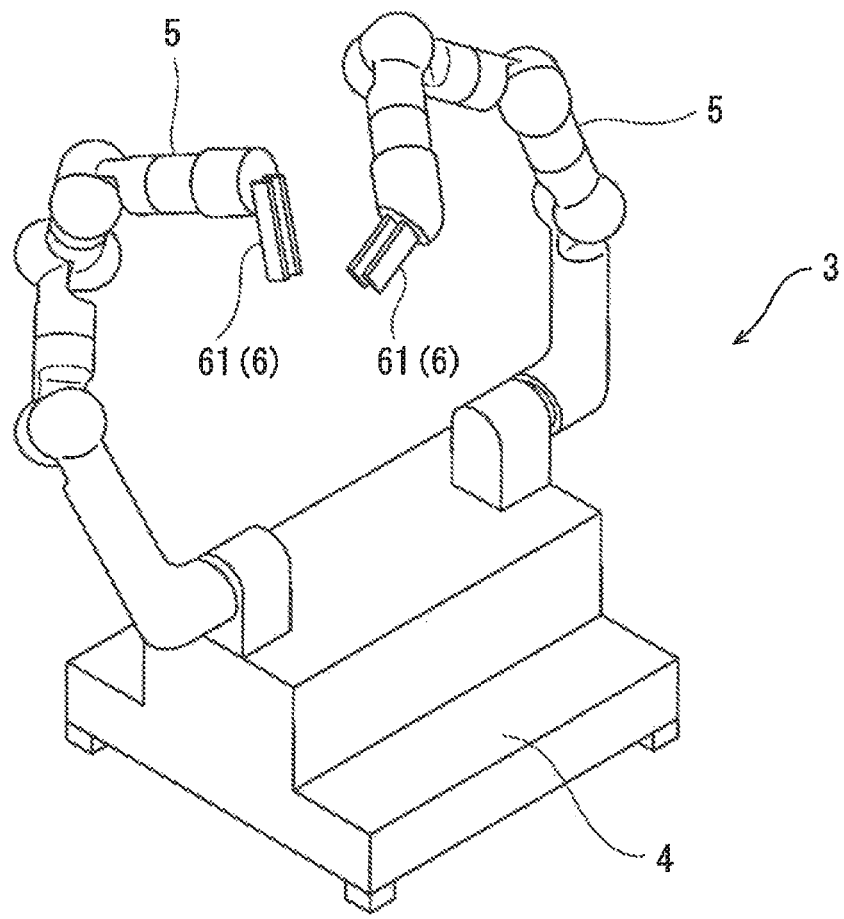
FIG. 1 is a perspective view of a robot in a robot system according to one embodiment of the present invention.
Figure 2:
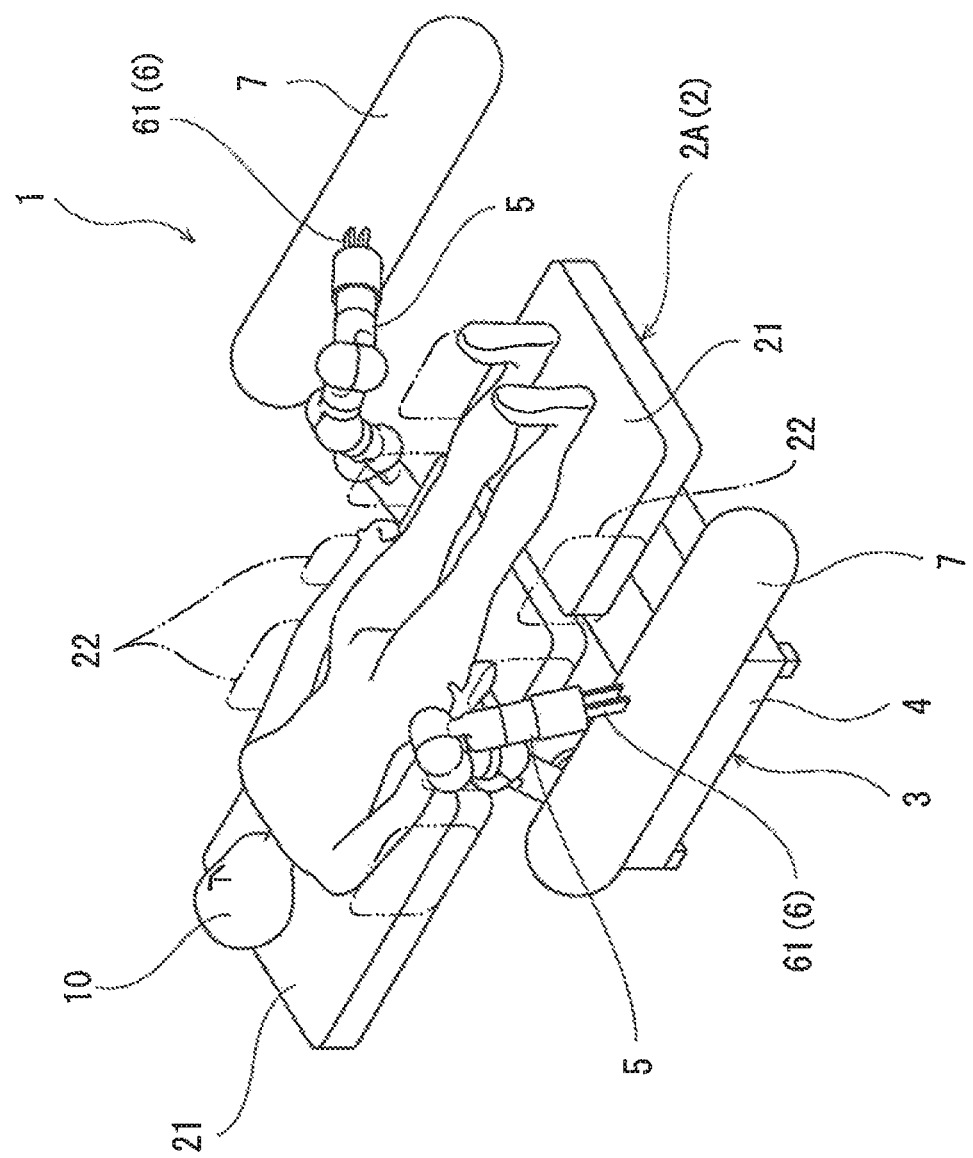
FIG. 2 is a perspective view of the robot system, the view showing one of the steps in the case of changing a body position.

FIGS. 2 to 13 show a robot system 1 according to one embodiment of the present invention. FIG. 1 shows a robot 3 included in the robot system 1. In the present embodiment, the robot 3 performs four nursing/medical actions on a person 10. The person 10 may be different for each of the nursing/medical actions.

Figure 5:
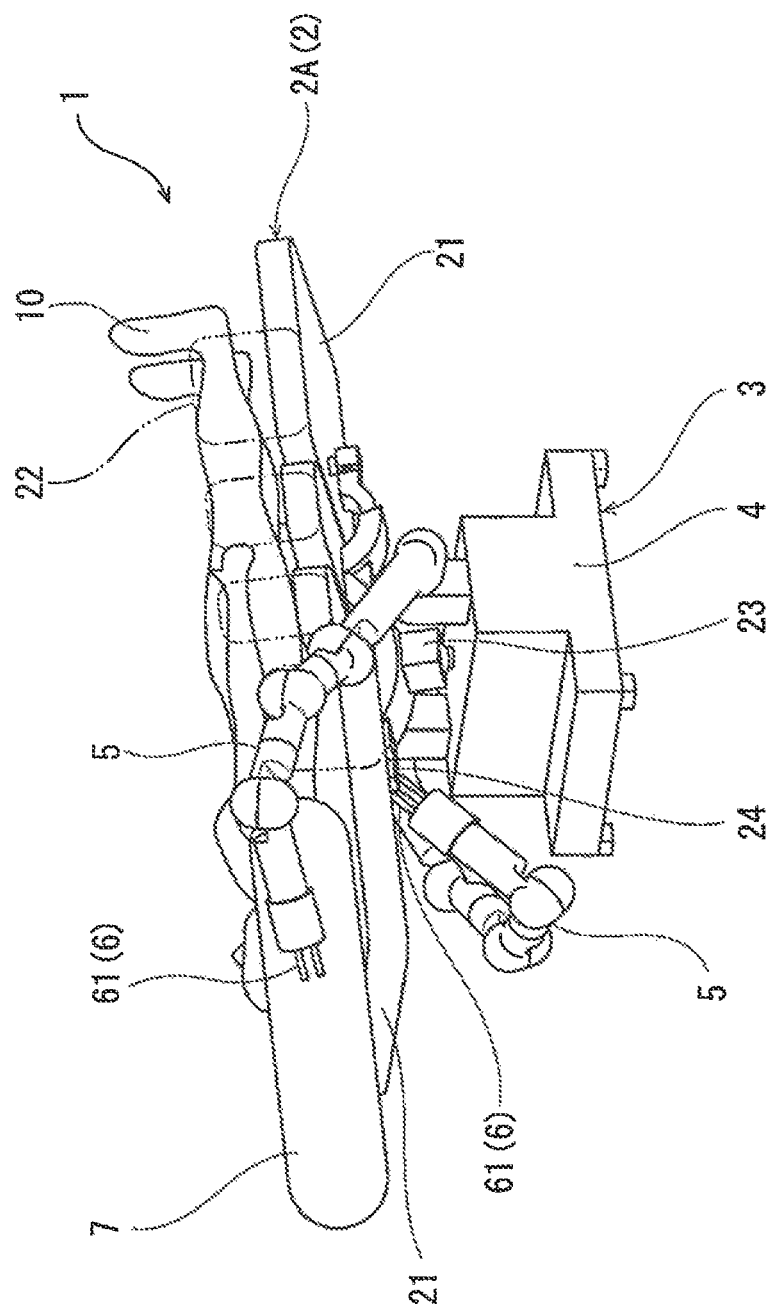
FIG. 5 is a perspective view of the robot system, the view showing one of the steps in the case of changing the body position.
Figure 6:
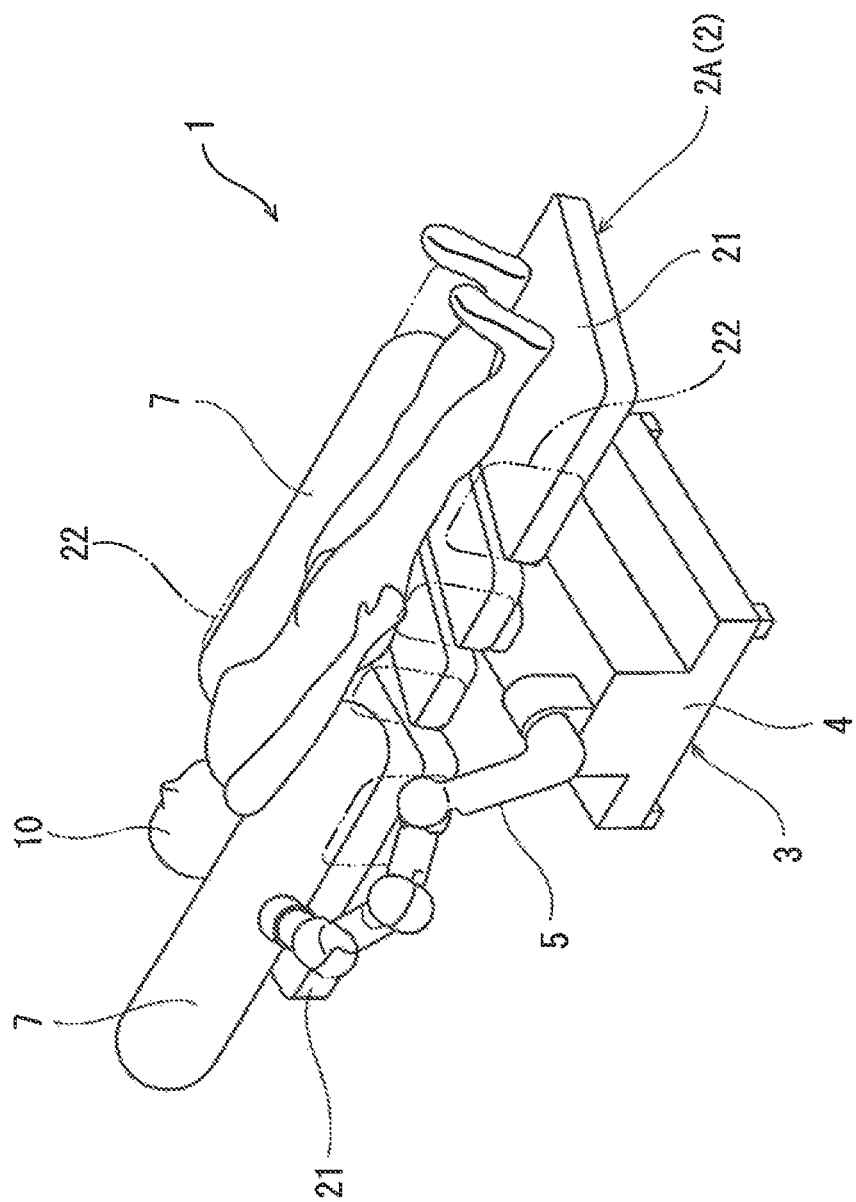
FIG. 6 is a perspective view of the robot system, the view showing one of the steps in the case of changing the body position.
Figure 7:
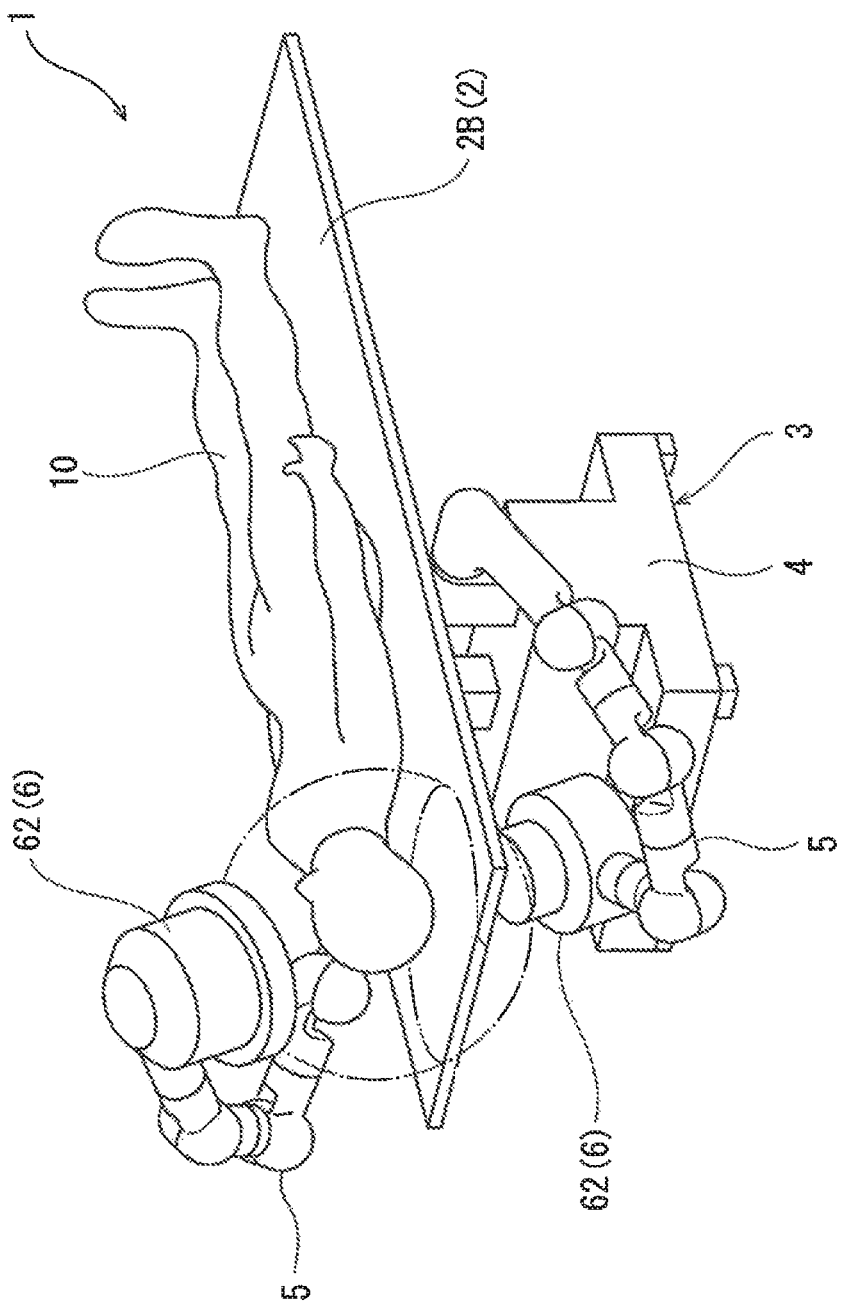
FIG. 7 is a perspective view of the robot system, the view showing one of the steps in the case of performing a transmission inspection.
Figure 8:
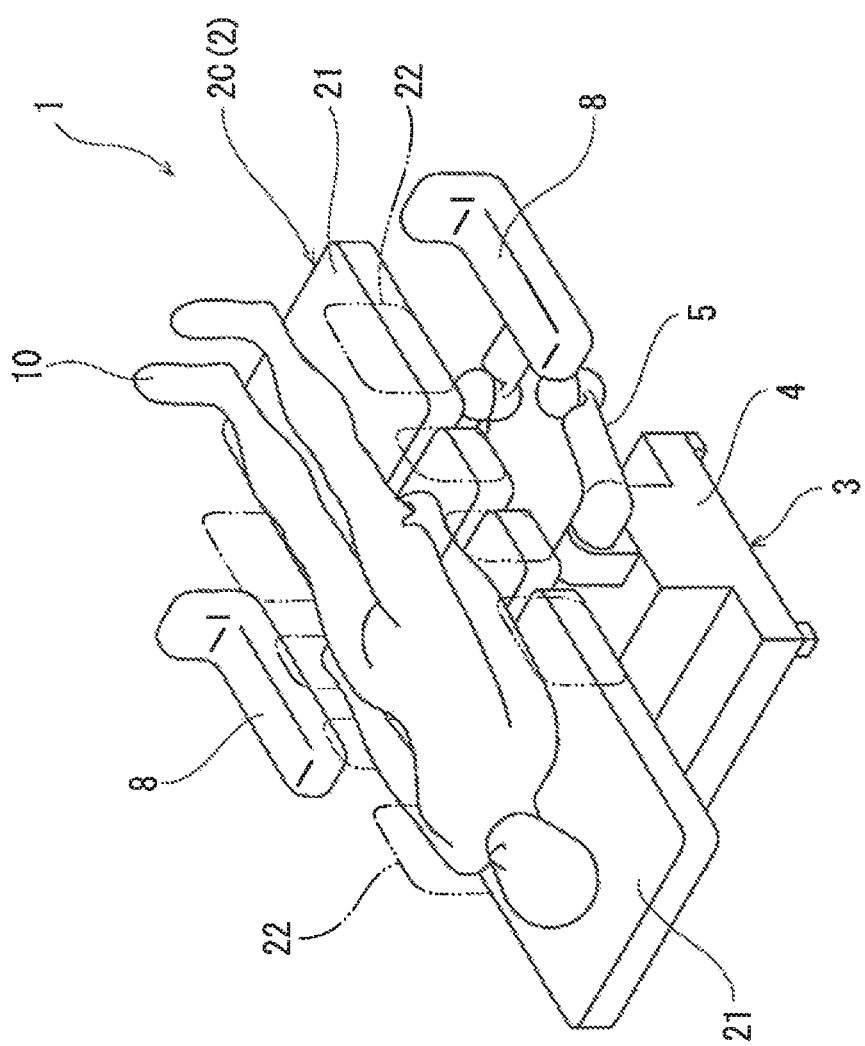
FIG. 8 is a perspective view of the robot system, the view showing one of the steps in the case of raising the upper half of the body.
Figure 9:
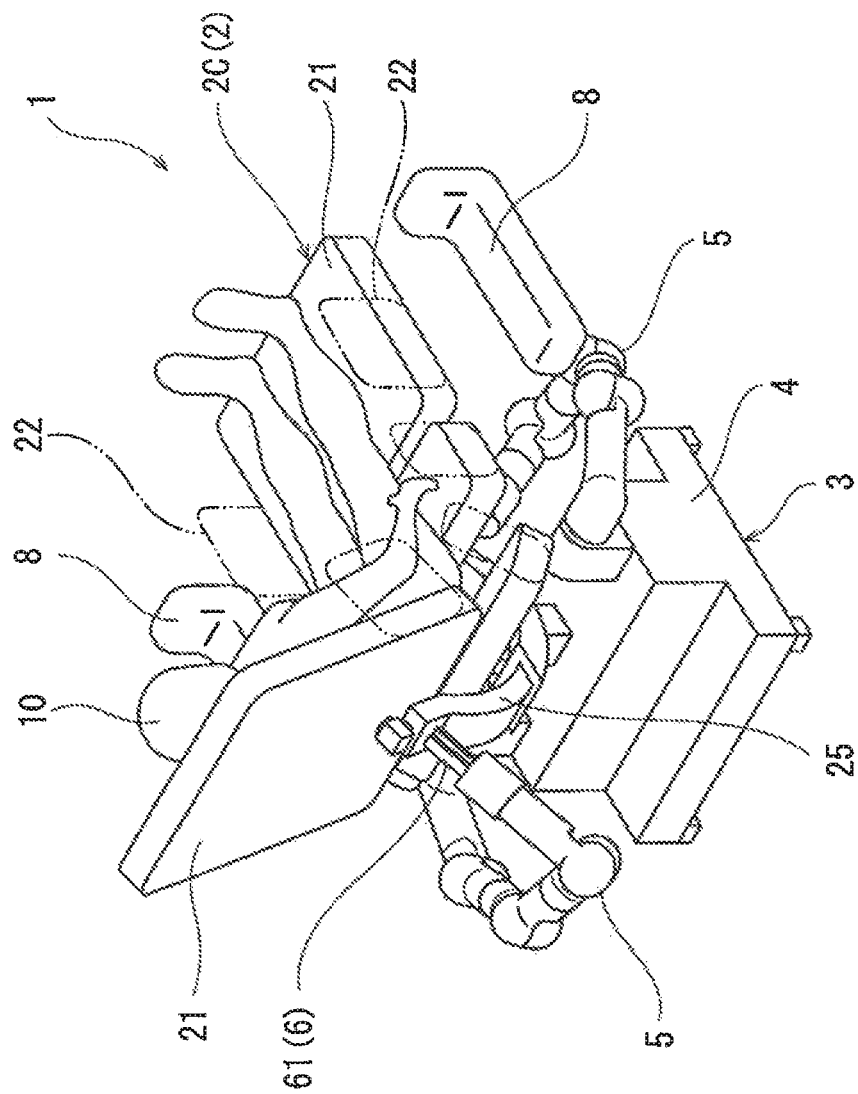
FIG. 9 is a perspective view of the robot system, the view showing one of the steps in the case of raising the upper half of the body.
Figure 10:
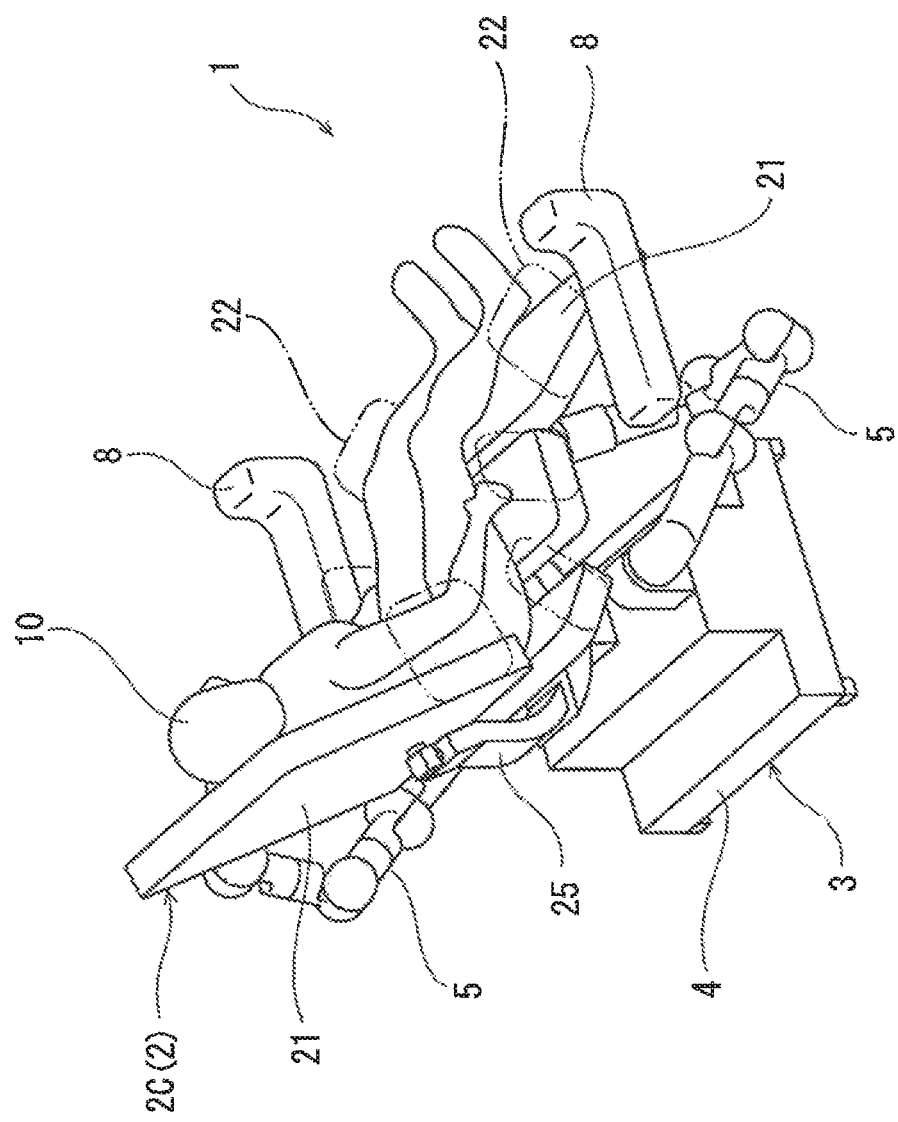
FIG. 10 is a perspective view of the robot system, the view showing one of the steps in the case of raising the upper half of the body.
Figure 11:
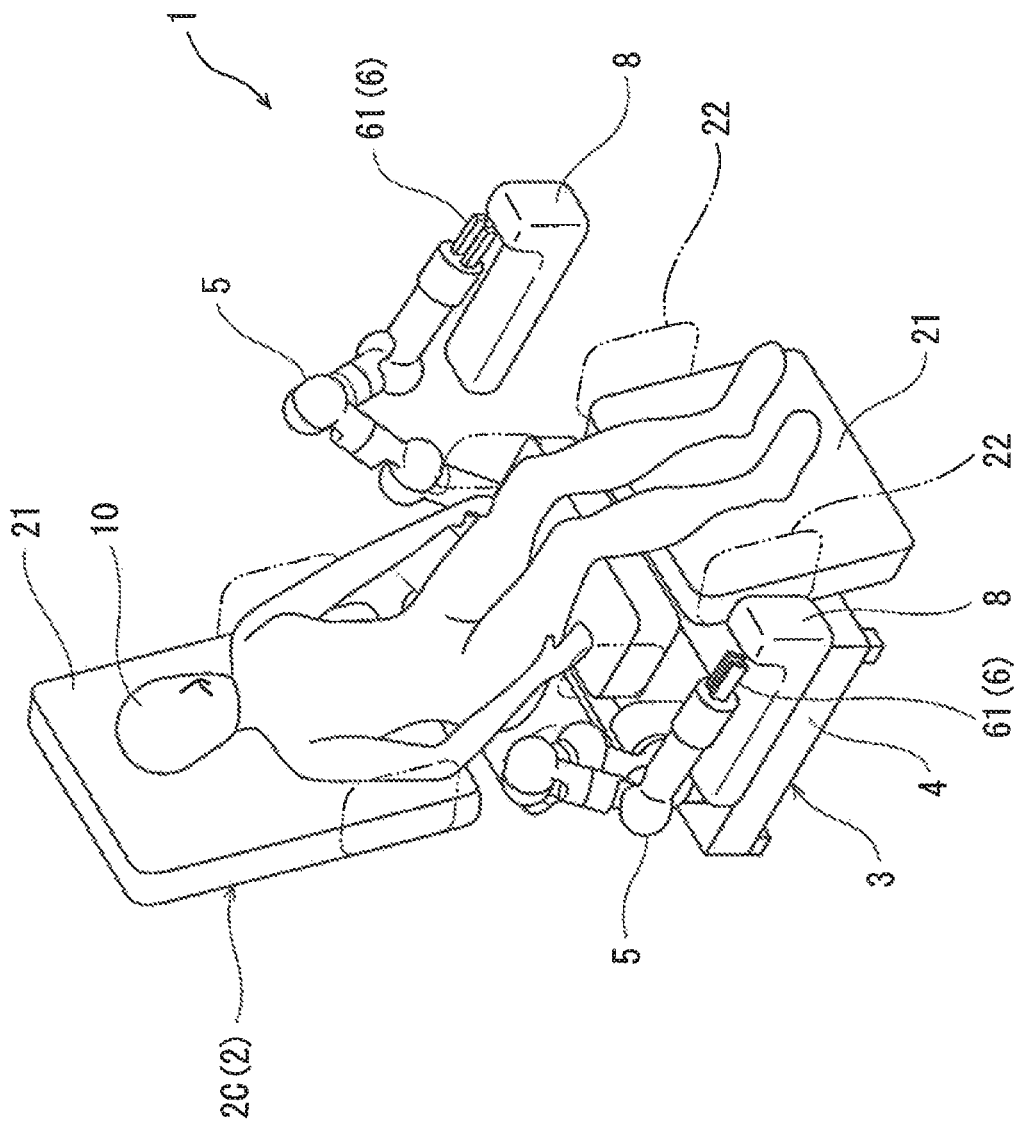
FIG. 11 is a perspective view of the robot system, the view showing one of the steps in the case of performing standing-up motion assistance.
Figure 12:
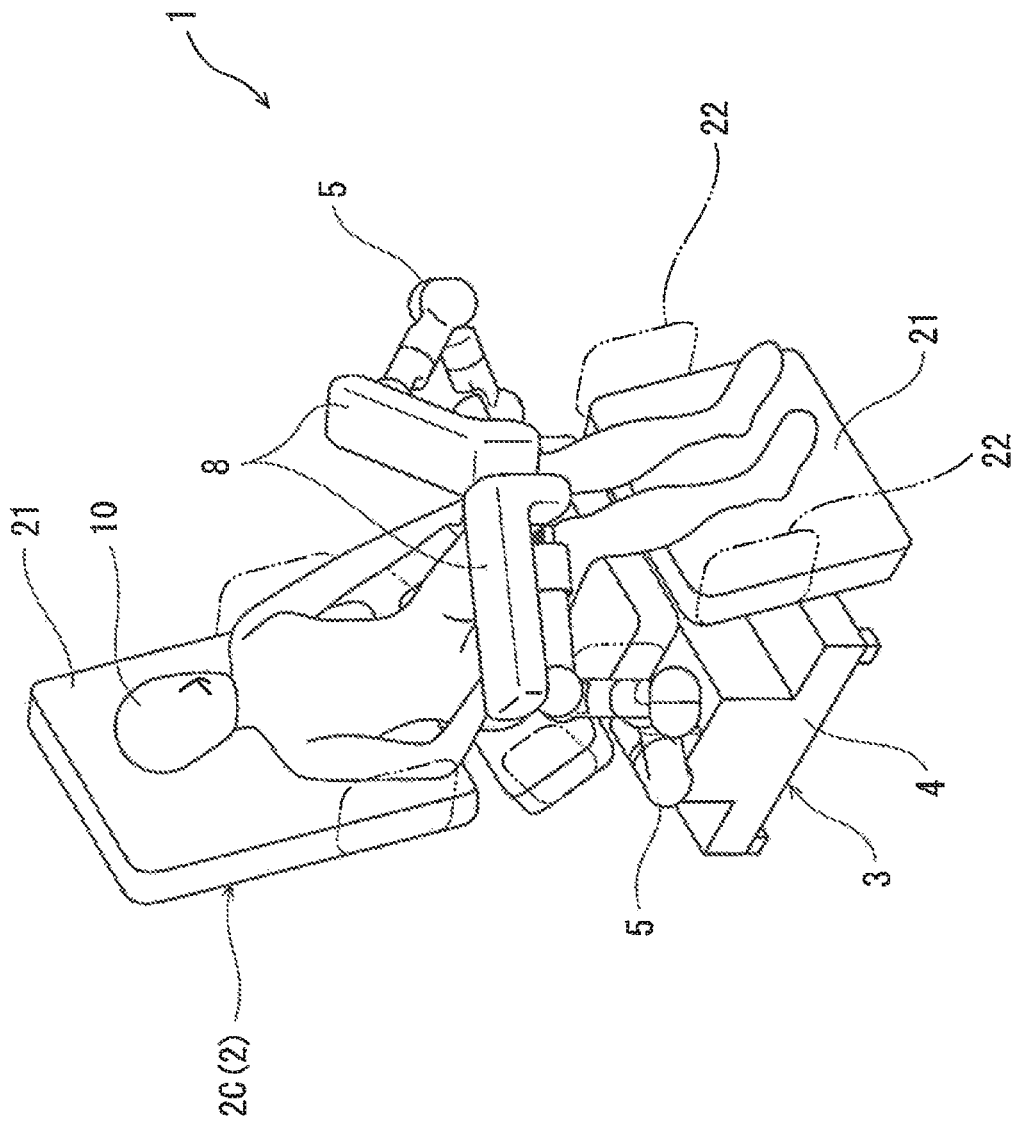
FIG. 12 is a perspective view of the robot system, the view showing one of the steps in the case of performing the standing-up motion assistance.
Figure 13:
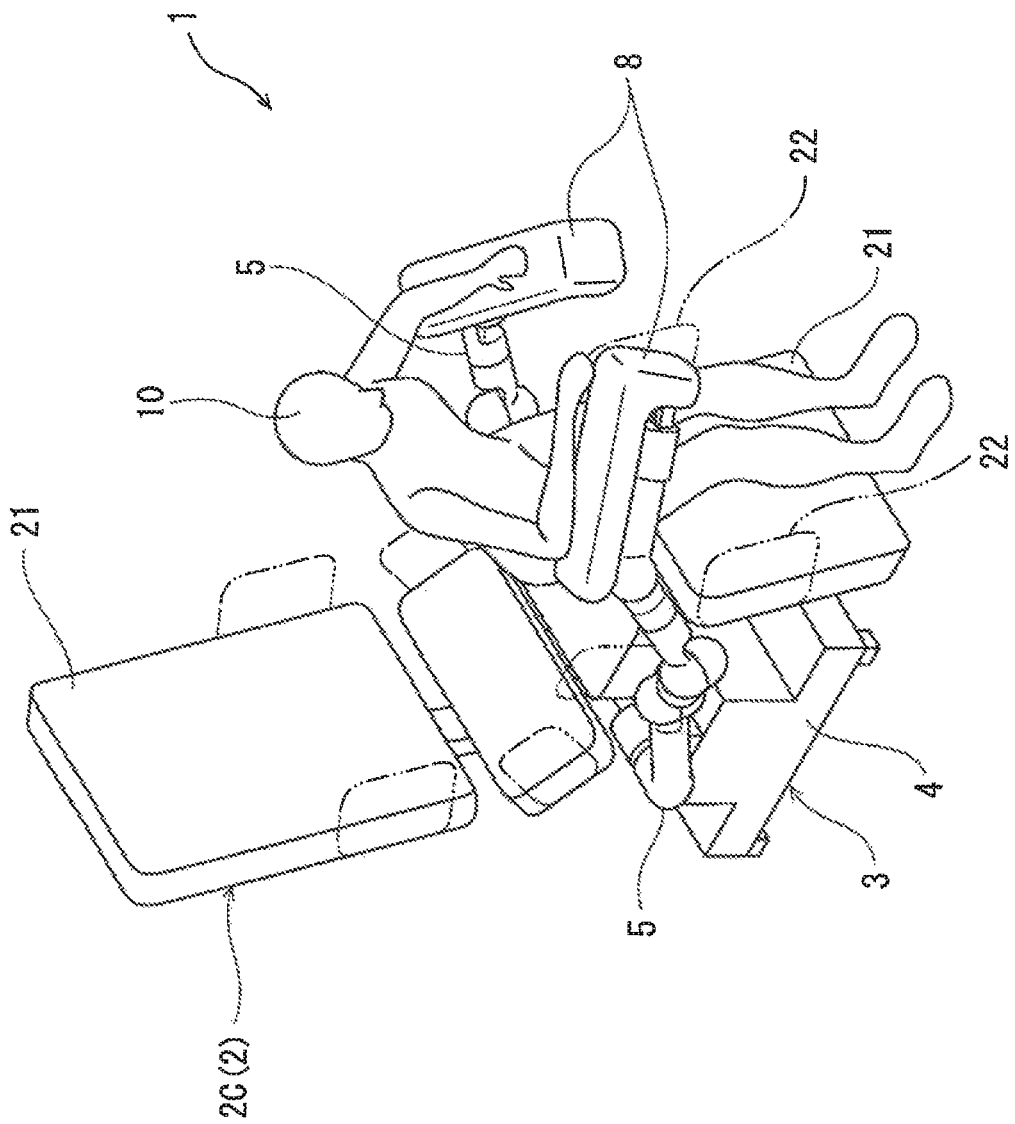
FIG. 13 is a perspective view of the robot system, the view showing one of the steps in the case of performing the standing-up motion assistance.

A first nursing/medical action is an action of changing the body position of the person 10 as shown in FIG. 2 to FIG. 6. For example, changing the body position may be performed during a medical operation or nursing care for the purpose of preventing bedsores. A second nursing/medical action is an action of performing a transmission inspection on the person 10 as shown in FIG. 7. A third nursing/medical action is an action of raising the upper half of the body of the person 10 as shown in FIG. 8 to FIG. 10. A fourth nursing/medical action is an action of performing standing-up motion assistance to the person 10 as shown in FIG. 11 to FIG. 13.

The robot system 1 includes: the robot 3; and three supporting units 2, on each of which the person 10 is placeable as shown in FIG. 2 to FIG. 13. The three supporting units 2 are: a transformable bed 2A shown in FIG. 2 to FIG. 6; a fixed bed 2B shown in FIG. 7; and a transformable bed 2C shown in FIG. 8 to FIG. 13.

As shown in FIG. 1, the robot 3 includes: a plurality of multi-jointed arms 5 each having a plurality of degrees of freedom; and at least one base 4 provided with the multi-jointed arms 5. Preferably, each of the multi-jointed arms 5 has at least six degrees of freedom (e.g., seven degrees of freedom). In the present embodiment, the number of bases 4 is one, and the number of multi-jointed arms 5 is two. However, as an alternative, the number of bases 4 may be two or more, and the number of multi-jointed arms 5 may be three or more.

In the present embodiment, the base 4 is disposed under the supporting unit 2 such that, during each of the four nursing/medical actions, the entirety of the base 4 is accommodated within the space occupied by the supporting unit 2. According to this configuration, since the relatively large base 4 of the robot 3 is concealed under the supporting unit 2, anyone around the supporting unit 2 can freely come close to the person 10 placed on the supporting unit 2. This allows anyone around the supporting unit 2 to readily perform a procedure/treatment (e.g., a medical operation or nursing care) on the person 10 placed on the supporting unit 2. It should be noted that the robot 3 may be configured to perform each of the four nursing/medical actions in accordance with a sound or an operation of a switch.

Further, in the present embodiment, the robot 3 is configured such that, during each of the four nursing/medical actions, the two multi-jointed arms 5 can be retracted under the supporting unit 2. Since the two multi-jointed arms 5 have such a retractable configuration, when the robot 3 performs no nursing/medical action, the multi-jointed arms 5 can be retracted under the supporting unit 2, and the robot 3 can be stored under the supporting unit 2.

A plurality of types (in the present embodiment, two types) of equipment 6 corresponding to the aforementioned nursing/medical actions are each removably mounted to the two multi-jointed arms 5. The robot 3 operates these different types of equipment 6 via the multi-jointed arms 5, thereby performing the four nursing/medical actions. Although not illustrated, information obtaining devices, such as a camera and a sensor, are attached to the robot 3. Based on information obtained from the information obtaining devices, the multi-jointed arms 5 are controlled by a robot control board 41 (see FIG. 14) built in the base 4.

The two types of equipment 6 are: a pair of hands 61 used for changing the body position and raising the upper half of the body of the person 10; and a pair of transmission inspection devices 62 used for performing the transmission inspection on the person 10. The pair of hands 61 is mounted to the two multi-jointed arms 5, such that each hand 61 is mounted to the distal end of a corresponding one of the multi-jointed arms 5. Alternatively, Instead of the hands 61, the pair of transmission inspection devices 62 is mounted to the two multi-jointed arms 5, such that each transmission inspection device 62 is mounted to the distal end of a corresponding one of the multi-jointed arms 5.

In the present embodiment, each of the three supporting units 2 (the transformable bed 2A, the transformable bed 2C, and the fixed bed 2B) is coupled to the base 4. Accordingly, the position of each supporting unit 2 relative to the base 4 of the robot 3 is fixed. This makes it possible to readily perform the positioning of the equipment 6, which is mounted to the multi-jointed arms 5, relative to the person 10 or the supporting unit 2. It should be noted that each supporting unit 2 is not necessarily coupled to the base 4, but any or all of the three supporting units 2 may be supported by a support pillar installed upright on a floor on which the robot 3 is placed.

Figure 14:
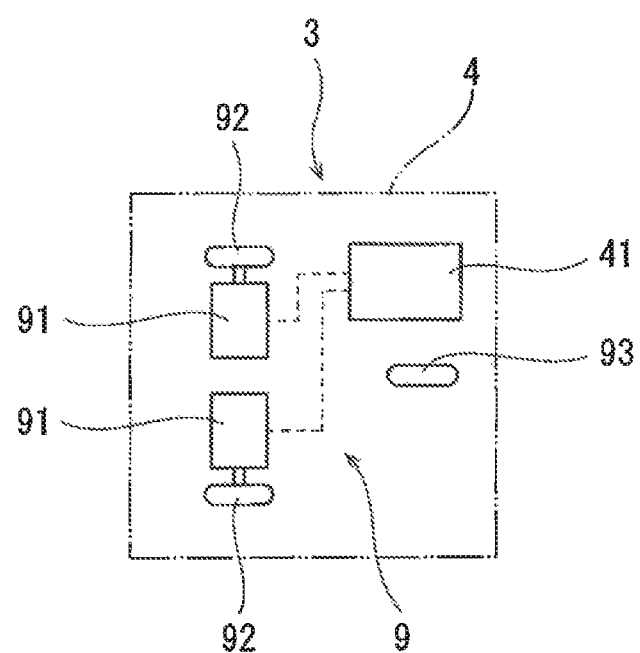
FIG. 14 is a bottom view of the robot, the view showing a moving device.

Desirably, the base 4 of the robot 3 is movable. For example, a moving device 9 as shown in FIG. 14 may be incorporated in the base 4. The moving device 9 includes: right and left wheels 92 to be driven; and a front wheel 93, which is a follower wheel. The moving device 9 further includes a pair of servomotors 91 configured to drive the right and left wheels 92. The robot 3 is moved by controlling the pair of servomotors 91 by the robot control board 41. This configuration makes it possible to freely run the robot 3. However, as an alternative, the base 4 of the robot 3 may be transferred by a transfer mechanism provided on the floor on which the robot 3 is placed.

Hereinafter, the aforementioned nursing/medical actions (changing the body position, performing the transmission inspection, raising the upper half of the body, and performing the standing-up motion assistance) are described in detail.

(Changing the Body Position)

As shown in FIG. 2 to FIG. 6, in the case of changing the body position, the transformable bed 2A, which is partly swingable in its width direction, is used as the supporting unit 2. Also, in the case of changing the body position, the hands 61 are mounted to both the multi-jointed arms 5, respectively. By operating the transformable bed 2A with the hands 61, the robot 3 changes the body position of the person 10 via the transformable bed 2A to change the positions where the person 10 is in contact with the transformable bed 2A.

As mentioned above, the transformable bed 2A is coupled to the base 4. In the present embodiment, the transformable bed 2A is coupled to the base 4 via a first swinging mechanism 23 (described below), which is disposed substantially at the center of the transformable bed 2A. The transformable bed 2A is supported by the base 4. However, as previously mentioned, the transformable bed 2A may be separated from the base 4.

The transformable bed 2A is divided in its longitudinal direction into a plurality of (in the illustrated example, four) pieces 21. Side rails 22 are provided on both ends of each piece 21 in its width direction. The four pieces 21 are configured such that the adjoining pieces 21 are rotatable relative to each other about an axis extending in the longitudinal direction of the transformable bed 2A.

Further, in the present embodiment, the entire transformable bed 2A is configured to be swingable in its width direction. The transformable bed 2A includes: the first swinging mechanism 23 (see FIG. 4) configured to swing the entire transformable bed 2A in its width direction; and a second swinging mechanism 24 (see FIG. 5) configured to swing each piece 21 in its width direction.

Still further, in the present embodiment, in the case of changing the body position, a pair of log-shaped cushions 7 for the person 10 is used. For example, each cushion 7 may be configured to expand into a predetermined shape when fed with a working fluid, such as water or air, and shrink when the working fluid is discharged therefrom. When the robot 3 performs no nursing/medical action, the cushions 7 may be shrunk and retracted under the transformable bed 2A together with the multi-jointed arms 5.

Figure 3:
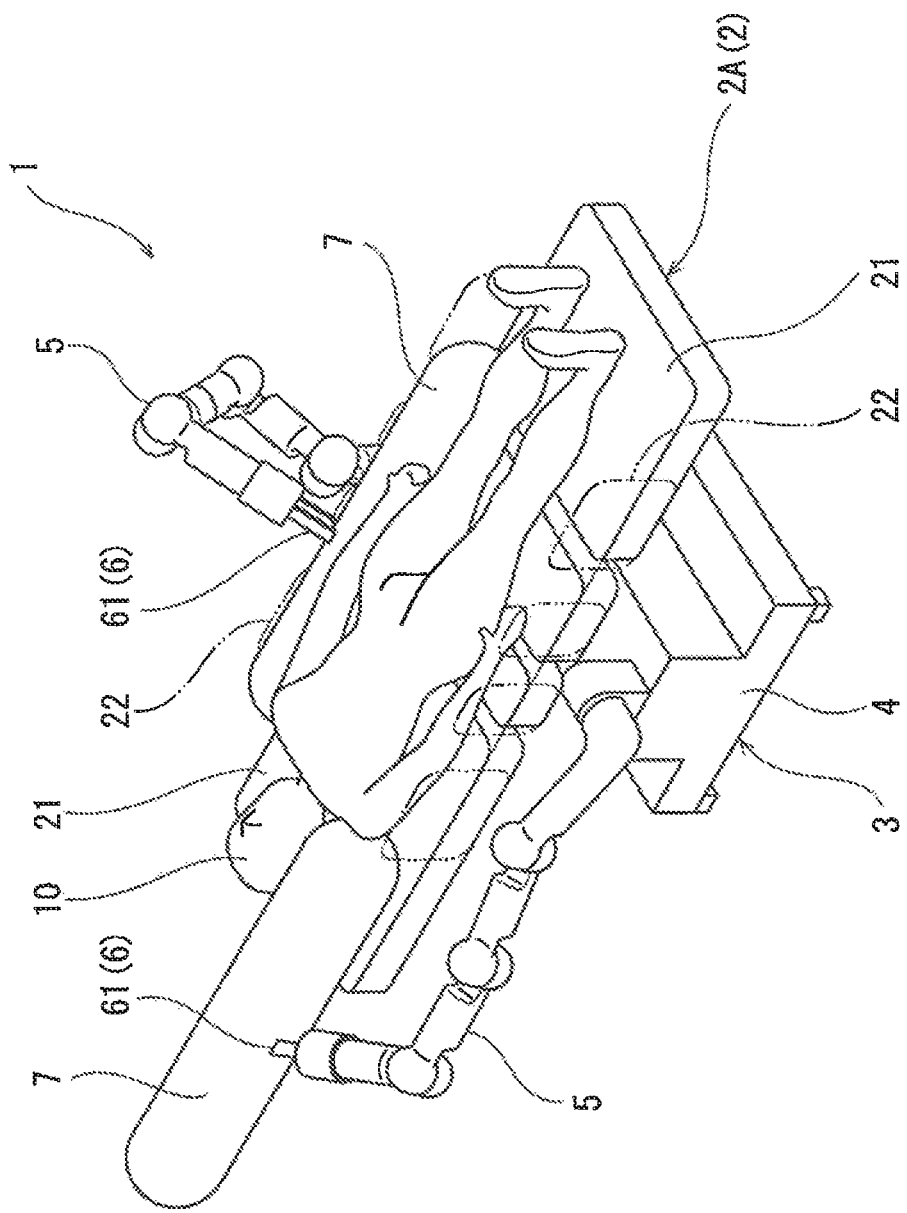
FIG. 3 is a perspective view of the robot system, the view showing one of the steps in the case of changing the body position.
Figure 4:
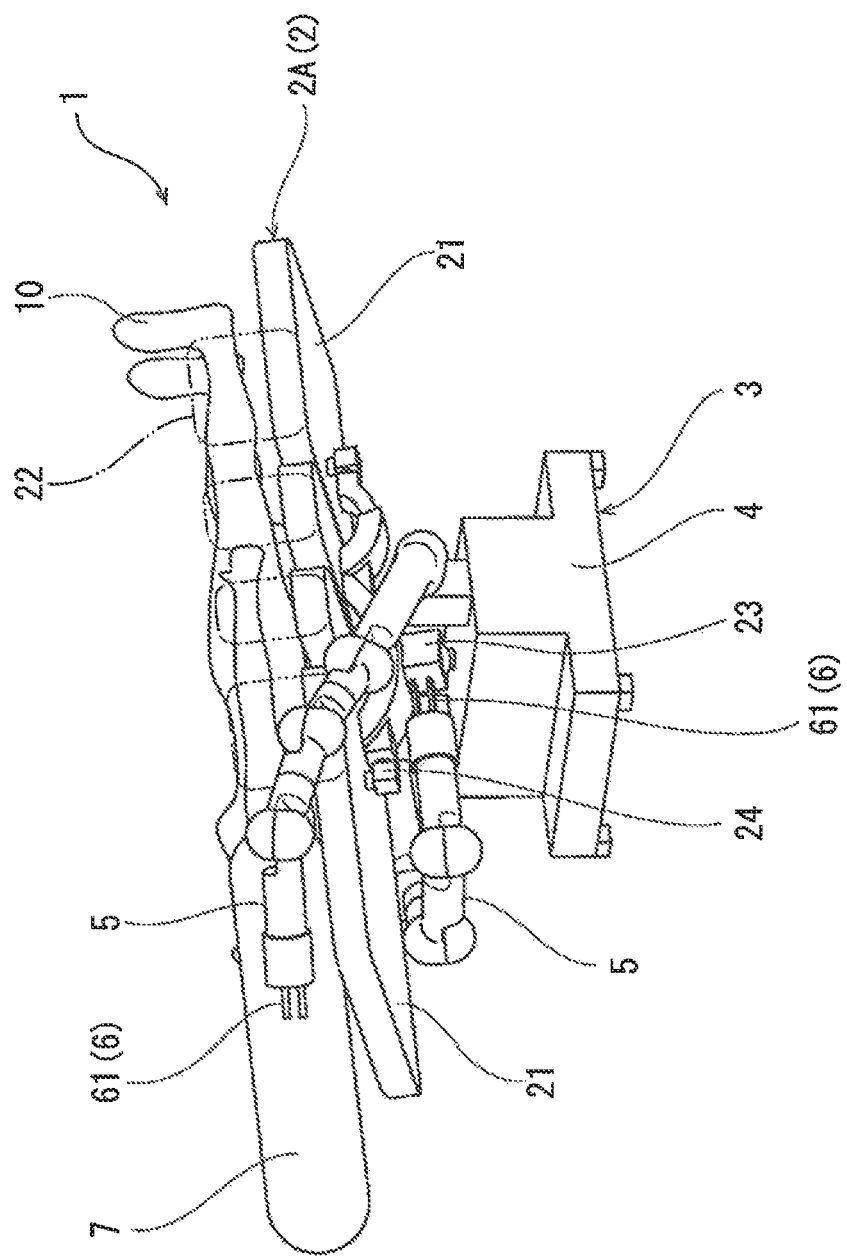
FIG. 4 is a perspective view of the robot system, the view showing one of the steps in the case of changing the body position.

First, the robot 3 grabs the cushions 7 with both hands 61, and as shown in FIG. 3, inserts one of the cushions 7 between the person 10 and the side rails 22. Then, as shown in FIG. 4, the robot 3 operates the first swinging mechanism 23 with one hand 61 to tilt the entire transformable bed 2A to the inserted cushion 7 side. Thereafter, as shown in FIG. 5, the robot 3 operates the second swinging mechanism 24 with the same hand 61 to bring one end piece 21 (on the head side of the person 10) back to the horizontal position. Subsequently, as shown in FIG. 6, the robot 3 inserts the other cushion 7 into a space formed between the one end piece 21 and the person 10 with the other hand 61.

It should be noted that changing the body position as shown in FIG. 2 to FIG. 6 is merely one example. Of course, changing the body position can be performed in a different manner. The same is true in the following cases of: performing the transmission inspection on the person 10; raising the upper half of the body of the person 10; and performing the standing-up motion assistance to the person 10, which will be described below. The robot 3 may be configured to repeat the action of changing the body position of the person 10 at predetermined intervals.

(Transmission Inspection)

As shown in FIG. 7, in the case of performing the transmission inspection, the fixed bed 2B is used as the supporting unit 2. Also, in the case of performing the transmission inspection, the transmission inspection devices 62 are mounted to both the multi-jointed arms 5, respectively. For example, one of the transmission inspection devices 62 emits an X-ray, and the other transmission inspection device 62 receives the X-ray. The robot 3 performs the transmission inspection by moving the pair of transmission inspection devices 62, for example, along a spherical path centered on the head of the person 10.

As mentioned above, the fixed bed 2B is coupled to the base 4. In the present embodiment, the fixed bed 2B is coupled to the base 4 substantially at the center of the fixed bed 2B and supported by the base 4. However, as previously mentioned, the fixed bed 2B may be separated from the base 4.

(Raising the Upper Half of the Body)

As shown in FIG. 8 to FIG. 10, in the case of raising the upper half of the body, the transformable bed 2C, which is transformable between a bed mode and a chair mode, is used as the supporting unit 2. Also, in the case of changing the body position, the hands 61 are mounted to both the multi-jointed arms 5, respectively. The robot 3 operates the transformable bed 2C with the hands 61, thereby raising the upper half of the body of the person 10 via the transformable bed 2C to change the state of the person 10 from a lying-down state into a sitting state. Armrests 8, which are used in the standing-up motion assistance (described below), are disposed on both sides of the transformable bed 2C, respectively.

As mentioned above, the transformable bed 2C is coupled to the base 4. In the present embodiment, the transformable bed 2C is coupled to the base 4 via a first raising/lowering mechanism 25 (described below), which is disposed substantially at the center of the transformable bed 2C. The transformable bed 2C is supported by the base 4. However, as previously mentioned, the transformable bed 2C may be separated from the base 4.

The transformable bed 2C is divided in its longitudinal direction into a plurality of (in the illustrated example, four) pieces 21. Side rails 22 are provided on both ends of each piece 21 in its width direction. The four pieces 21 are configured such that the adjoining pieces 21 are rotatable relative to each other about their respective axes extending in the width direction of the transformable bed 2C. The transformable bed 2C includes: the first raising/lowering mechanism 25 (see FIG. 9) configured to raise/lower the two pieces 21 on the head side of the person 10; and a second raising/lowering mechanism (not shown) configured to raise/lower the two pieces 21 on the foot side of the person 10.

When the transformable bed 2C is in the bed mode as shown in FIG. 8, all of the pieces 21 are horizontal. First, as shown in FIG. 9, the robot 3 operates the first raising/lowering mechanism 25 with one hand 61 to put the two pieces 21 on the head side in a standing state. Then, as shown in FIG. 10, the robot 3 operates the second raising/lowering mechanism with the other hand 61 to put the two pieces 21 on the foot side in a hanging state.

(Standing-Up Motion Assistance)

As shown in FIG. 11 to FIG. 13, in the case of performing the standing-up motion assistance, the armrests 8 are attached to both the multi-jointed arms 5, respectively. However, as an alternative, the armrest 8 may be attached to only one of the multi-jointed arms 5. The robot 3 performs the standing-up motion assistance to support the person 10 with the armrests 8 until the person 10 in the sitting state stands up.

Specifically, first, as shown in FIG. 11, the robot 3 attaches the armrests 8 to distal-end arm portions of the respective multi-jointed arms 5 with the hands 61. Then, as shown in FIG. 12, the robot 3 moves both the armrests 8 to the front of the chest of the person 10. Thereafter, the robot 3 opens up the armrests 8 as the person 10 stands up.

For example, each armrest 8 may be configured by using the cushion 7 described above. To be more specific, the interior of the cushion 7, which expands or shrinks due to the working fluid, may be segmented into a plurality of cells, and the working fluid may be fed to one of the cells to realize the shape of the armrest 8. When the robot 3 performs no nursing/medical action, the armrests 8 may be shrunk and retracted under the transformable bed 2C together with the multi-jointed arms 5.

As described above, the robot system 1 of the present embodiment is capable of using the robot 3 as a platform for a plurality of nursing/medical actions. This makes it possible to perform the plurality of (in the present embodiment, four) nursing/medical actions with the single robot 3. In other words, the robot 3 can be used in common for the four nursing/medical actions.

<Variations>

The present invention is not limited to the above-described embodiment. Various modifications can be made without departing from the spirit of the present invention.

For example, the robot 3 may be configured to perform at least two medical actions. Accordingly, the nursing/medical actions to be performed by the robot 3 may be two or three actions among the four nursing/medical actions of the above-described embodiment. As one example, in a case where the robot 3 is configured to only perform the action of changing the body position and the action of raising the upper half of the body, the robot system 1 may only include the hands 61 as the equipment 6. Thus, the robot system 1 may include at least one type of equipment 6.

As another example, in a case where the robot 3 is configured to only perform the action of raising the upper half of the body and the action of performing the standing-up motion assistance, the robot system 1 may only include the transformable bed 2C as the supporting unit 2. Thus, the robot system 1 may include at least one supporting unit 2.

Alternatively, the supporting unit 2 having a combination of functions, specifically, a combination of the function of the transformable bed 2A of being partly swingable in the width direction and the function of the transformable bed 2C of being transformable between the bed mode and the chair mode, may be used.

The nursing/medical actions to be performed by the robot 3 are not limited to the nursing/medical actions described in the above embodiment. Examples of other nursing/medical actions performable by the robot 3 include assisting rehabilitation, massaging, and assisting eating. Various types of equipment 6 can be mounted to the multi-jointed arms 5 of the robot 3 in accordance with the nursing/medical actions to be performed by the robot 3.

REFERENCE SIGNS LIST 1 robot system
10 person
2 supporting unit
2A, 2C transformable bed
3 robot
4 base
41 robot control board
5 multi-jointed arm
6 equipment
61 hand
62 transmission inspection device
8 armrest
9 moving device
91 servomotor
92, 93 wheel

The invention claimed is:

1. A robot system comprising:
at least one supporting unit, on which a person is placeable;
a robot including a plurality of multi-jointed arms, each of which has a plurality of degrees of freedom, and at least one base provided with the plurality of multi-jointed arms; and
at least one type of equipment mountable to the plurality of multi-jointed arms, wherein
the robot is configured to perform at least two nursing/medical actions on the person by operating the at least one type of equipment,
the at least one type of equipment includes a cushion,
the robot is configured to expand the cushion by feeding a working fluid to the cushion, and shrink the cushion by discharging the working fluid from the cushion, and
the at least two nursing/medical actions include an action of changing a body position of the person by using the cushion.

2. The robot system according to claim 1, wherein
the at least one type of equipment includes a pair of transmission inspection devices that are mounted to two multi-jointed arms, respectively, of the plurality of multi-jointed arms, and
the at least two nursing/medical actions include an action of performing a transmission inspection on the person.

3. The robot system according to claim 1, wherein
the at least one supporting unit includes a transformable bed partly swingable in its width direction,
the at least one type of equipment includes a hand configured to operate the transformable bed, and
the at least two nursing/medical actions include an action of changing a body position of the person via the transformable bed to change a position where the person is in contact with the transformable bed.

4. The robot system according to claim 1, wherein
the at least one supporting unit includes a transformable bed transformable between a bed mode and a chair mode,
the at least one type of equipment includes a hand configured to operate the transformable bed, and
the at least two nursing/medical actions include an action of raising an upper half of a body of the person via the transformable bed to change a state of the person from a lying-down state into a sitting state.

5. The robot system according to claim 4, further comprising an armrest attached to at least one of the plurality of multi-jointed arms, wherein
the at least two nursing/medical actions include an action of performing standing-up motion assistance to the person to support the person with the armrest until the person in the sitting state stands up.

6. The robot system according to claim 1, wherein
the at least one type of equipment includes a plurality of types of equipment, and
each type of equipment is removably mounted to the plurality of multi-jointed arms.

7. The robot system according to claim 1, wherein
the at least one supporting unit is coupled to the at least one base.

8. The robot system according to claim 1, wherein
the at least one base is disposed under the supporting unit, such that an entirety of the at least one base is accommodated under a space occupied by the supporting unit.

9. The robot system according to claim 1, wherein
the robot is configured such that the plurality of multi-jointed arms are retractable under the at least one supporting unit.

10. The robot system according to claim 1, wherein
the robot is configured to perform each of the at least two nursing/medical actions in accordance with a sound or an operation of a switch.

11. The robot system according to claim 1, wherein
the robot is configured to repeat the action of changing the body position of the person at predetermined intervals.

12. The robot system according to claim 1, further comprising a moving device incorporated in the base, the moving device including a pair of servomotors configured to drive right and left wheels, wherein
the robot is moved by controlling the pair of servomotors by a robot control board.

13. The robot system according to claim 1, wherein
when the robot performs no nursing/medical action, the robot is configured to retract the multi-jointed arms under the at least one supporting unit, with the cushion in a shrunk state.

* * * * *